(12) United States Patent
Konstorum (10) Patent No.: US 8,579,801 B2
(45) Date of Patent: Nov. 12, 2013

(54) ENDOSCOPE RIVETED DEFLECTION SECTION FRAME

(75) Inventor: Gregory S. Konstorum, Stamford, CT (US)

(73) Assignee: Gyrus ACMI, Inc., Southborough, MA (US)

( * ) Notice: Subject to any disclaimer, the term of this patent is extended or adjusted under 35 U.S.C. 154(b) by 1085 days.

(21) Appl. No.: 12/462,805

(22) Filed: Aug. 10, 2009

(65) Prior Publication Data
US 2011/0034772 A1 Feb. 10, 2011

(51) Int. Cl.
*A61B 1/00* (2006.01)

(52) U.S. Cl.
USPC ............ 600/142; 600/128; 600/139; 600/141

(58) Field of Classification Search
USPC .................................. 600/141, 142, 128, 139
See application file for complete search history.

(56) References Cited

U.S. PATENT DOCUMENTS

| | | | |
|---|---|---|---|
| 5,178,129 A * | 1/1993 | Chikama et al. | 600/142 |
| 2005/0245789 A1 | 11/2005 | Smith et al. | 600/159 |
| 2007/0270679 A1* | 11/2007 | Nguyen et al. | 600/373 |
| 2009/0156995 A1* | 6/2009 | Martin et al. | 604/95.04 |
| 2010/0056868 A1* | 3/2010 | Kitagawa | 600/142 |

* cited by examiner

*Primary Examiner* — Philip R Smith
*Assistant Examiner* — Rynae Boler
(74) *Attorney, Agent, or Firm* — Harrington & Smith (57) ABSTRACT

An endoscope deflection section frame including a plurality of rings and rivets. Each ring has front ears and rear ears with rivet holes through the ears. The rivets are located in the rivet holes to thereby pivotably connect the rings to one another. Each rivet includes a head at an interior side of an inner one of the ears and an opposite end at an exterior side of an outer one of the ears. The opposite end is welded to the outer ear.

9 Claims, 7 Drawing Sheets

ENDOSCOPE RIVETED DEFLECTION SECTION FRAME

BACKGROUND OF THE INVENTION

1. Field of the Invention

The invention relates to an endoscope and, more particularly, to a frame of a deflection section of an endoscope.

2. Brief Description of Prior Developments

U.S. Patent Publication No. 2005/0245789 A1 discloses an endoscope having a shaft frame with pivotably connected members. There is a conventional endoscope shaft riveted deflection system construction that consists of a number of deflection rings connected together with rivets. Each rivet has a first head. Each rivet is inserted into corresponding holes of joining rings from inside the deflection system, and then a second head is formed from outside during the assembly.

There is another riveted deflection construction used in a Storz Flex-X Flexible Ureteroscope where the cylindrical body of each rivet is welded to an inner ear flat surface of one of the deflection rings, and each rivet has only one head located outside the deflection system frame. The conventional construction having a rivet with two heads is less torque resistant than the Storz construction; due to the clearance between the rivet body and the two deflection ring holes. In the conventional construction having a rivet with two heads it is difficult to control rivet cylindrical body dimensions (of the rivet shaft section) to maintain guaranteed clearance between the rivet head and the two deflections rings due to the force applied to form the second rivet head. In the Storz construction, it is difficult to maintain guaranteed clearance due to welding the rivet to the inner ear flat surface of one of the deflection rings because the welding process requires pressing the rivet to the ring ear flat surface by force, this can deform the ring which can result in a clearance problem remaining after welding. Thus, there is a desire to provide a different method of manufacture and resultant shaft frame which has better guaranteed clearance among the rivet and frame rings.

SUMMARY

The following summary is merely intended to be exemplary. The summary is not intended to limit the scope of the claimed invention.

In accordance with one aspect of the invention, an endoscope deflection section frame is provided including a plurality of rings and rivets. Each ring has front ears and rear ears with rivet holes through the ears. The rivets are located in the rivet holes to thereby pivotably connect the rings to one another. Each rivet includes a head at an interior side of an inner one of the ears and an opposite end at an exterior side of an outer one of the ears. The opposite end is welded to the outer ear.

In accordance with one aspect of the invention, a method is provided comprising aligning rivet holes of two endoscope deflection section frame members with each other; inserting a fastener into the holes; and welding the fastener to an exterior side of one of the rings to thereby pivotably attach the rings to each other.

In accordance with one aspect of the invention, a method is provided comprising aligning rivet holes of two endoscope deflection section frame rings with each other; inserting a rivet into the holes, wherein a head of the rivet is located at an interior side of a first one of the rings and an opposite second end of the rivet extends to an exterior side of a second one of the rings; inserting a mandrel into the rings, wherein the mandrel aligns the rings relative to each other and contacts the head of the rivet to align the rivet relative to the rings, maintaining a required clearance between the rivet head and the inner ring ear; and fixedly connecting the rivet to the second ring.

BRIEF DESCRIPTION OF THE DRAWINGS

The foregoing aspects and other features of the invention are explained in the following description, taken in connection with the accompanying drawings, wherein.

DETAILED DESCRIPTION OF EMBODIMENT

Figure 1:
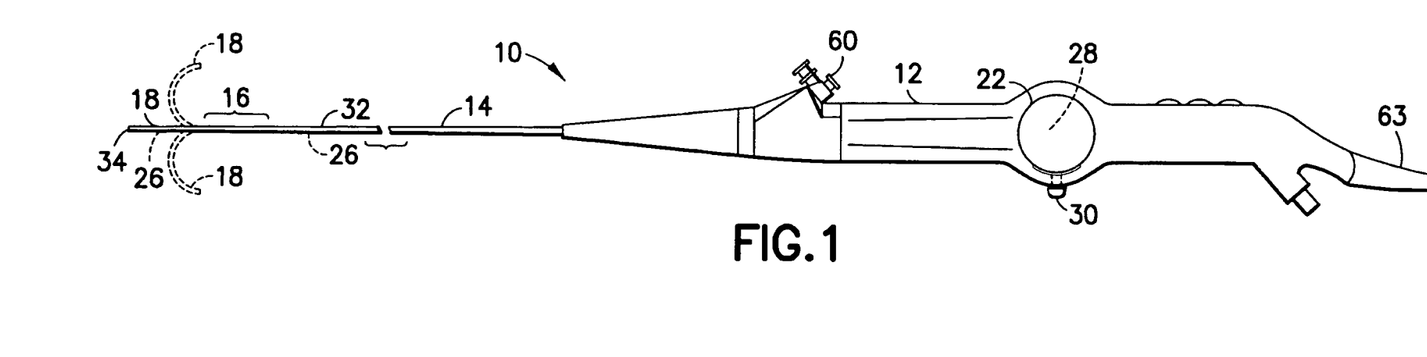
FIG. 1 is an elevational side view of an endoscope comprising features of the invention.

Referring to FIG. 1, there is shown a side view of an endoscope 10 incorporating features of the invention. Although the invention will be described with reference to the example embodiment shown in the drawings, it should be understood that the invention can be embodied in many alternate forms of embodiments. In addition, any suitable size, shape or type of elements or materials could be used.

The endoscope 10 is a ureteroscope. However, in alternate embodiments the endoscope could be any suitable type of endoscope. The endoscope 10 generally comprises a handle or control 12 and a flexible or semi-flexible shaft 14 connected to the handle 12. A deflection section (or steering section) is located at a distal end of the shaft 14. The deflection section, in this example embodiment, includes a passive deflection section 16 and an active deflection section 18. A control system 22 to control the active deflection section 18 extends from the handle 12 to the active deflection section 18. The control system 22 can comprise, for example, a pair of control wires, two wire sheaths, and an actuator 28. One end of the wires are connected to the actuator 28 and an opposite second end of the wires are connected to the distal end of the active deflection section 18.

In the preferred embodiment, the handle 12 has a user operated slide or lever 30. The lever 30 is connected to the actuator 28. The actuator 28 is adapted to pull and release the two wires of the control system 22. When the lever 30 is moved by the user, the actuator 28 is moved. The actuator 28 may be a drum or pulley, for example, rotatably connected to the handle 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the handle can have additional actuators and corresponding controls to drive the additional pairs of control wires to bend the deflection section in different plane(s). In still other alternate embodiments, the handle may have knobs with rack and pinion mechanisms or other suitable user operated controls for the control system.

The shaft 14 is cantilevered from the handle 12. The flexible shaft 14 and the deflection section include the control wires of the control system 22, a fiber optical image bundle or video sensor electrical cable, a working channel, and a fiber optical illumination bundle or electrical wires to illumination LEDs or lights at the objective head 34. A port 60 for inserting accessory instruments (not shown) into the working channel is located on the handle 12. The handle 12 also has an electrical cable 63 for connection to another device, such as a video monitor for example. In an alternate embodiment, instead of the cable 63, the endoscope could have an eyepiece. In alternate embodiments, the flexible shaft may house different systems within.

The deflection section or steering/articulation section generally comprises a frame 26, a cover 32 and the objective head 34. The cover 32 also extends over the shaft 14. However, in an alternate embodiment the deflection section may have a different softer cover. Referring also to FIGS. 2-6, at least one portion of the frame 26 generally comprises a plurality of rings 36 and connectors 38. The connectors 38 connect the rings 36 to adjacent rings. The rings 36 are preferably comprised of stainless steel. However, the rings could be comprised of another material such as plastic or a shape memory alloy material, such as Tinel or Nitinol for example.

Figure 2:
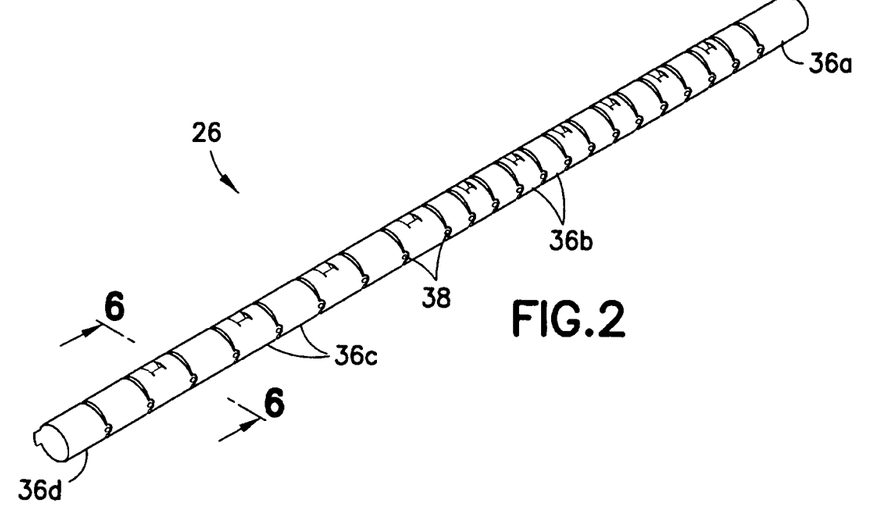
FIG. 2 is a perspective view of a portion of the frame used in the active deflection section of the endoscope shown in FIG. 1.

The rings 36 each comprise a one-piece member, but could be comprised of multiple members. The frame 26 shown in FIG. 2 is located at the very distal end of the shaft 14 and the passive deflection section 16. Features of the invention could also be used at other locations of the shaft 14 or the passive section 16 as well. In this embodiment the frame 26 comprises two different types of rings; short rings 36b and long rings 36c. The frame 26 also comprises an objective head coupler 36a for connecting the frame 26 to the objective head, and a shaft coupler 36d for coupling the frame 26 to the frame of the shaft or the passive deflection section. However, in alternate embodiment more or less than four types of rings could be provided. In addition, the rings could have different shapes and sizes.

Figure 3:
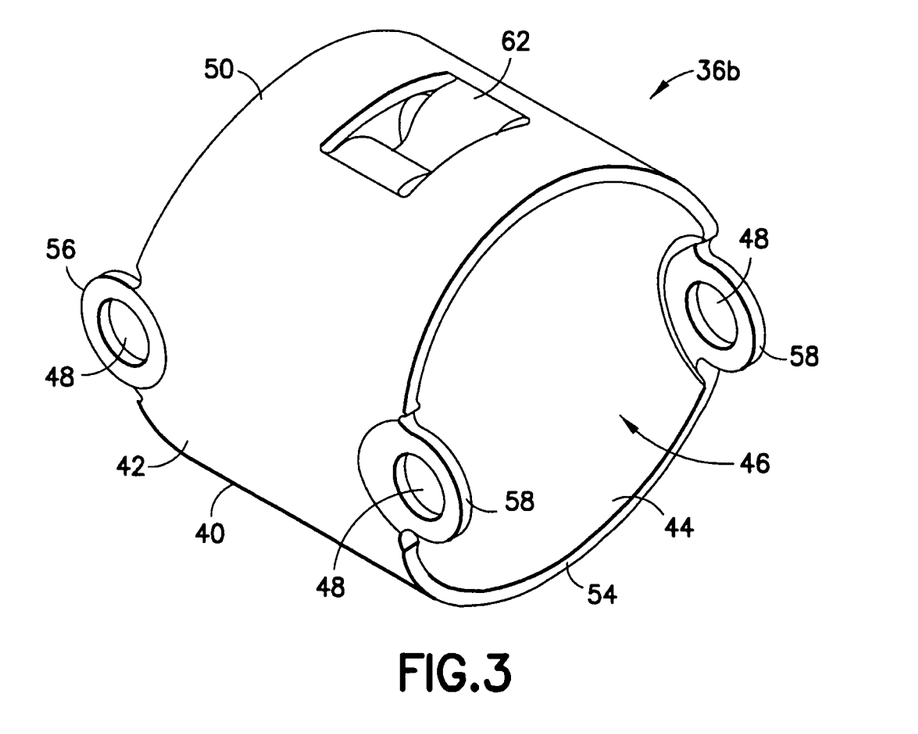
FIG. 3 is a perspective view of on of the frame member rings used in the frame shown in FIG. 2.
Figure 4:
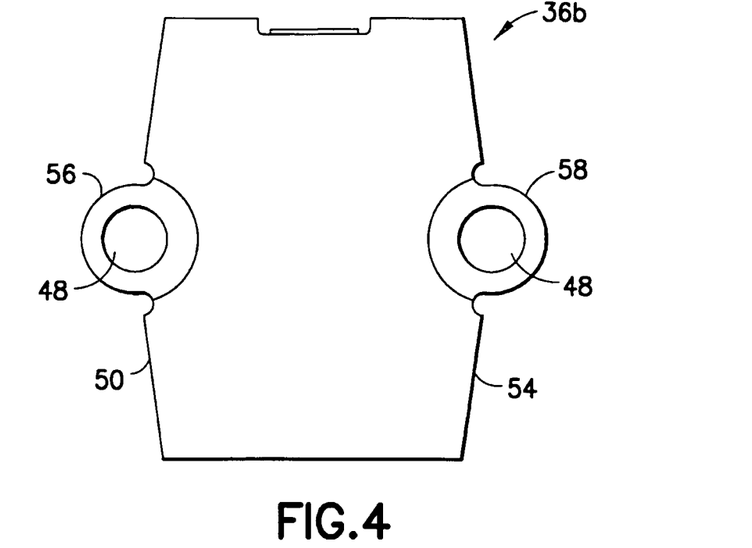
FIG. 4 is a side elevational view of the ring shown in FIG. 3.
Figure 5:
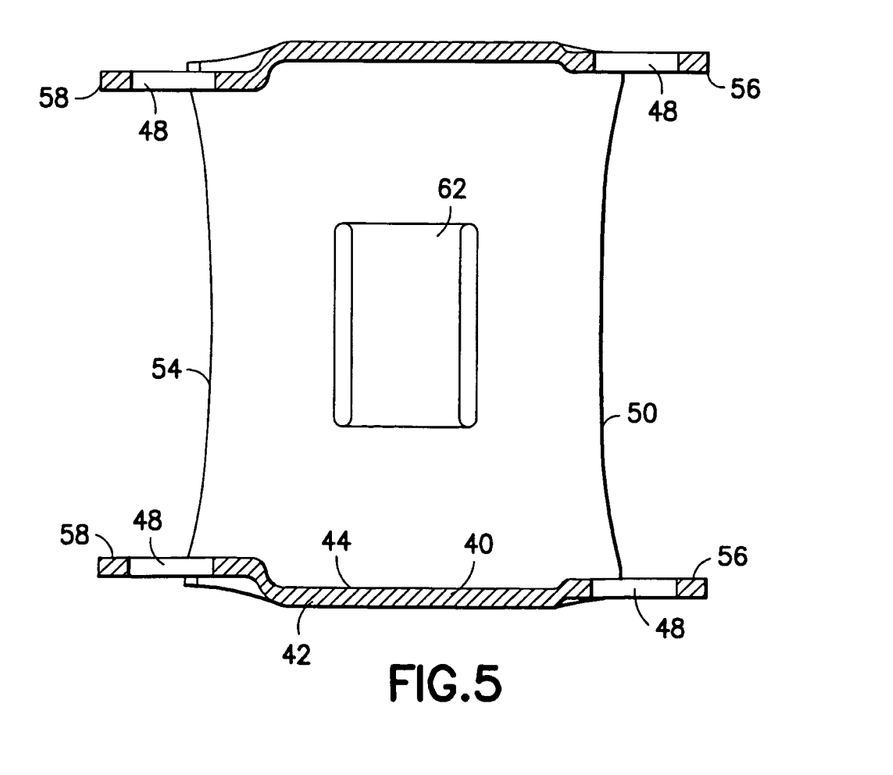
FIG. 5 is a cross sectional view of the ring shown in FIGS. 3-4.
Figure 6:
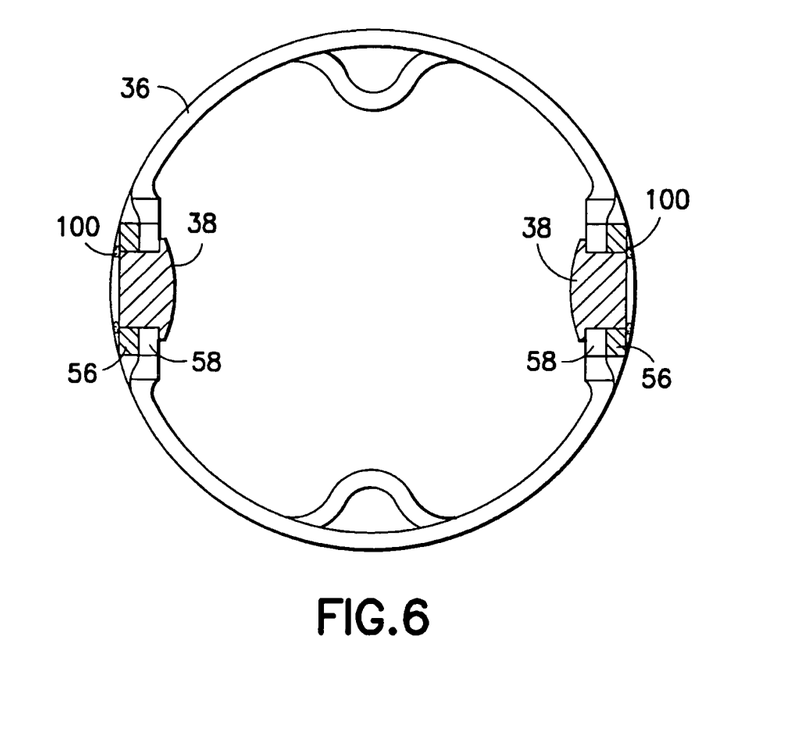
FIG. 6 is a cross sectional view of the frame shown in FIG. 2 taken along line 6-6.

With particular reference to FIGS. 3-5, one of the short rings 36b is shown and will be used to explain the features of the rings as an example. Each ring 36 has a wall 40 forming a central channel 46. The wall 40 has an exterior side 42 and an interior side 44. The wall 40 forms a front side at a front end 50 of the ring, and a rear side at a rear end 54 of the ring. The rings each comprise connector ears or projections 56, 58 which extend from the front and rear ends 50, 54. Each ear has a rivet hole 48. In this embodiment, the short rings 36b and long rings 36c have both front ears 56 and rear ears 58. The proximal ring 36d merely comprises front ears. The distal ring 36a merely comprises rear ears. As seen in FIG. 6, when the ears 56, 58 of a joining pair of rings are assembled, the front ears 56 form outer ears and the rear ears 58 form inner ears. The short and long rings include an indent feature 62 on one side which is sized and shaped for supporting a control cable.

Figure 7:
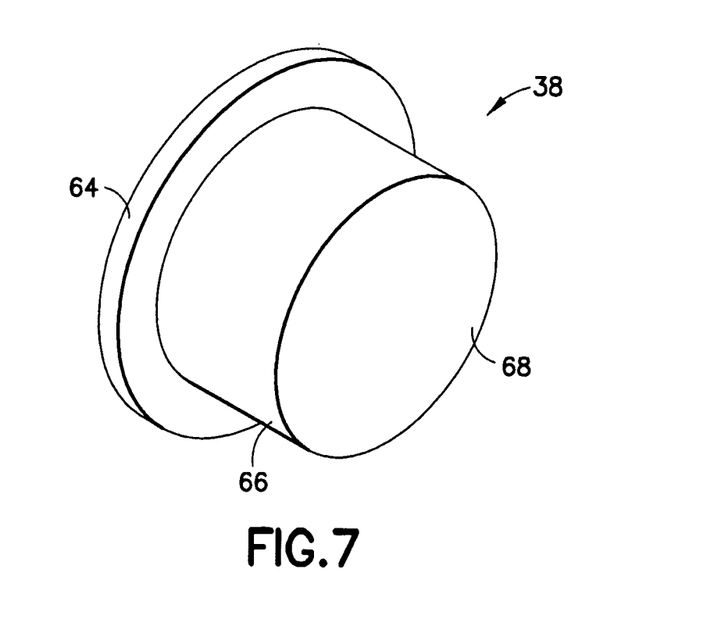
FIG. 7 is a perspective view of one of the rivet used in the frame shown in FIG. 2.
Figure 8:
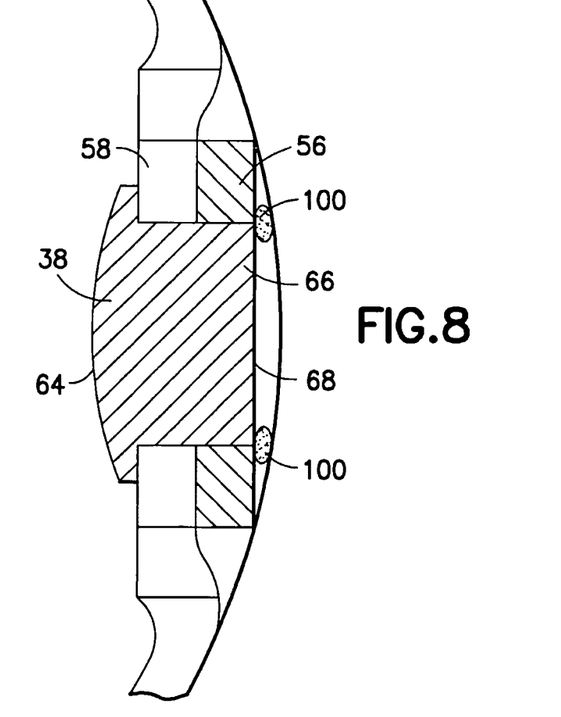
FIG. 8 is an enlarged view of a portion of the frame shown in FIG. 6.

FIG. 7 shows one of the rivets 38 before assembly into the frame 26. The rivet 38 has a head 64 and a rivet body 66. Referring also to FIG. 8, the rivets 38 are inserted into a pair of aligned rivet holes 48 of a pair of ears 56, 58 from two adjacent rings. More specifically, in this embodiment the rivet is inserted from inside the deflection section (from inside the central channel 46). Thus, the head 64 is located against the interior side of the inner ear 58. The end surface 68 of the rivet body 66 is located proximate the exterior surface of the outer ear 56.

The rivet 38 is fixedly, stationarily attached to the outer ear 56, such as by a weld 100 for example. In an alternate embodiment an additional or alternative connection could be provided, such as use of additional adhesive or a mechanical interlock for example. However, in the embodiment shown the end surface 68 is preferably welded to the exterior surface of the outer ear 56. The inner ear 58 is rotatably captured between the head 64 of the rivet and the outer ear 56.

The proposed riveted deflection system construction can use rivets with only one head. Each rivet can be inserted into the two joining rings' holes from inside the rings, and the rivets can be supported with a mandrel inserted inside the rings. After the entire deflection system (with rings and rivets assembled) is located on the mandrel, each rivet can be laser welded to the corresponding deflection ring outer ear.

Because each rivet is inserted from inside the rings and supported with the mandrel, there is no need to apply any force or pressure that might deform the ears or rivets. The mandrel also prepositions the rings and rivets prior to welding to insure proper positioning to the designed clearances. Thus, this can result in a guaranteed or assured clearance or tolerance (as designed) of the deflection rings and rivets assembly. Also, the proposed construction is more torque stable than the conventional rivet with two heads construction. With the invention, clearance between the rivet and only one joined ring is necessary at the rivet joint.

Figure 12:
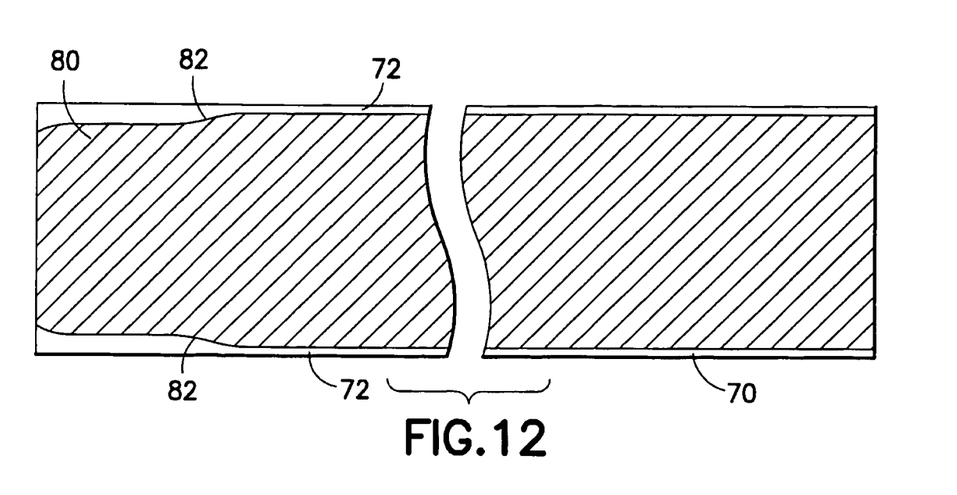
FIG. 12 is a cross sectional view of the mandrel shown in FIG. 11 taken along line 12-12.
Figure 13:
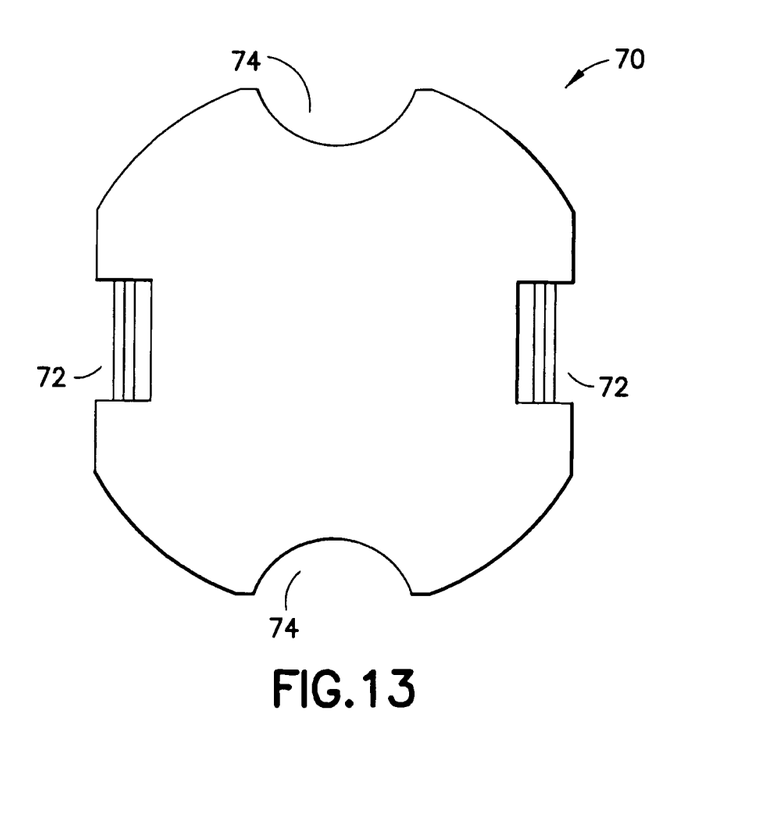
FIG. 13 is an elevational end view of the mandrel shown in FIGS. 11-12.

Referring also to FIGS. 9-13, one method of manufacturing the frame 26 can comprise use of a mandrel 70. The mandrel is a rod or bar, such as made of metal for example. The mandrel 70 has grooves 72 which are sized and shaped to receive the heads 64 of the rivets. In this embodiment the mandrel 70 also has grooves 74 to accommodate the indent features 62. The front of the rivet groove 72 has a tapered shape in this embodiment. Referring particularly to FIG. 12, in one method of the invention a first endoscope deflection frame ring is placed on a first end 80 of the mandrel 70 with the inner ears 58 of the ring facing towards the first end 80. Two rivets 38 are inserted into the rivet holes 48 of the inner ears 58, wherein the head 64 of each rivet is located at an interior side of the inner ears. A second endoscope deflection frame ring is located on the first end 80 of the mandrel with the outer ears on the inner ears of the first ring. The rivet holes of the inner ear of the first ring are aligned with the rivet holes of the outer ear of the second ring. The first and second rings are slid on the mandrel 70 from the front end wherein the rivet heads 64 are pushed by cam features 82 on the mandrel to move the body of each rivet into the rivet holes of the outer ears of the second ring. The rivets are then fixedly connected to the second ring, such as by welding.

Figure 9:
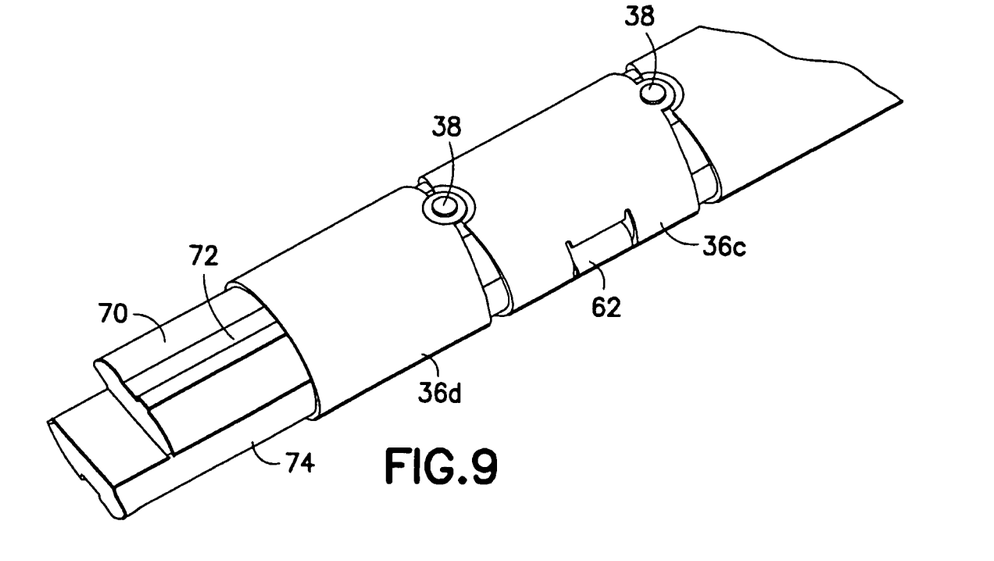
FIG. 9 is a perspective view of a mandrel being used to pre-assembly the rings and rivets of the frame shown in FIG. 2 prior to welding of the rivets to the rings.
Figure 10:
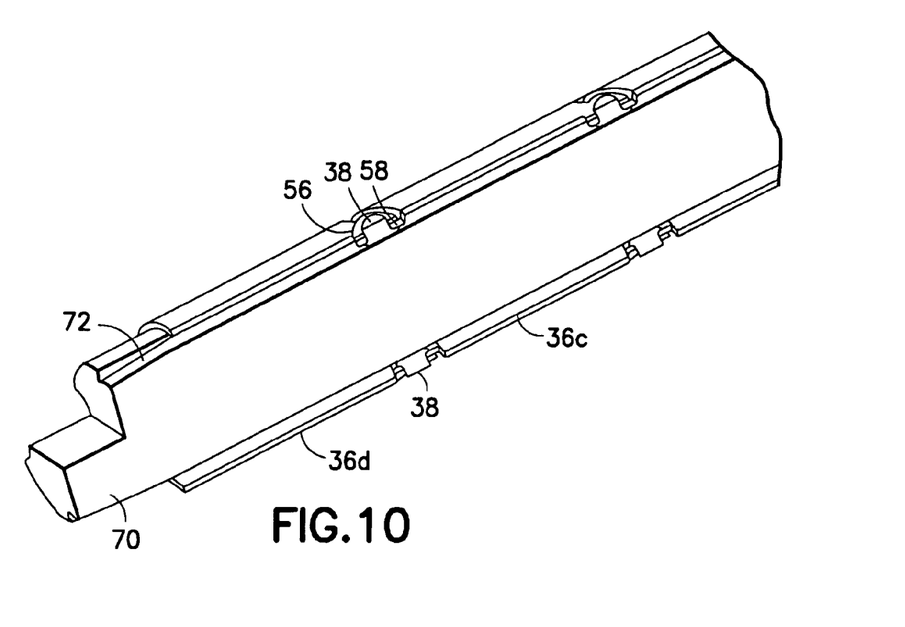
FIG. 10 is cross sectional view of the assembly shown in FIG. 9.
Figure 11:
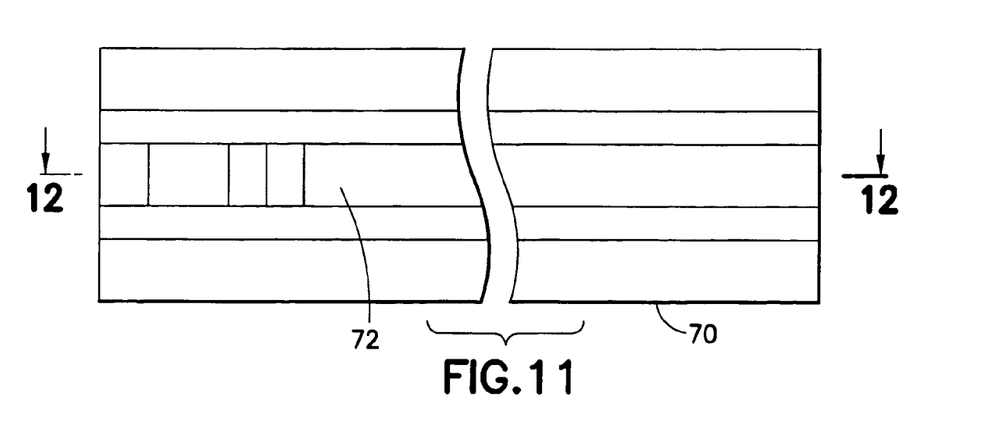
FIG. 11 is a elevational side view of the mandrel shown in FIGS. 9-10.

The rings 36 and rivets 38 are assembled on the mandrel 70 with the heads 64 of the rivets being pushed into a predetermined position relative to the rings 36 by the mandrel 70. The method can comprise aligning the rivet holes of two frame members with each other; inserting a rivet into the holes; and welding the rivet to an exterior side of one of the frame members to thereby pivotably attach the frame members to each other. The rivet is not deformed to connect the frame members, except by the welding. Inserting the fastener into the holes comprises inserting the rivet body from an interior of the frame members to locate the head against an interior side of one of the frame members. Welding the fastener comprises welding an end of the rivet body to the exterior side of one of the rings. The mandrel aligns the frame members relative to each other and contacts the head of the fastener to align the fastener relative to the frame members. The mandrel comprises channels receiving the indent features.

The method can comprise aligning rivet holes of two endoscope deflection frame rings with each other; inserting a rivet into the holes, wherein a head of the rivet is located at an interior side of a first one of the rings and an opposite second end of the rivet extends to an exterior side of a second one of the rings; inserting a mandrel into the rings, wherein the mandrel aligns the rings relative to each other and contacts the head of the rivet to align the rivet relative to the rings; and fixedly connecting the rivet to the second ring. Fixedly connecting the rivet to the second ring can comprise welding the rivet to the second ring. The rivet is not deformed to connect the rings, except by the welding. The rivet holes are located in front and rear ears extending from the rings. The rings comprise an indent feature on one side which is sized and shaped for supporting a control cable, and wherein the mandrel comprises channels receiving the indent features. The mandrel comprises a groove which slidably receives the head of the rivet. The groove has different depths to thereby cam the rivet into the holes as the mandrel is longitudinally slide into the rings.

It should be understood that the foregoing description is only illustrative of the invention. Various alternatives and modifications can be devised by those skilled in the art without departing from the invention. For example, features recited in the various dependent claims could be combined with each other in any suitable combination(s). In addition, features from different embodiments described above could be selectively combined into a new embodiment. Accordingly, the invention is intended to embrace all such alternatives, modifications and variances which fall within the scope of the appended claims.

What is claimed is:

1. A method comprising:
    placing a first endoscope deflection frame ring on a first end of a mandrel with an inner ear facing the first end of the mandrel;
    inserting a rivet into a rivet hole of the first ring, wherein a head of the rivet is located at an interior side of the inner ear;
    placing a second endoscope deflection frame ring on the first end of the mandrel with an outer ear on the inner ear of the first ring;
    aligning rivet holes of the inner ear of the first ring with rivet holes of the outer ear of the second ring;
    moving the first and second rings on the mandrel from the front end wherein the rivet head is pushed by a cam feature on the mandrel to move a body of the rivet in the rivet hole of the second ring; and
    fixedly connecting the rivet to the second ring.

2. A method as in claim 1 wherein fixedly connecting the rivet to the second ring comprises welding the rivet to the second ring.

3. A method as in claim 1 wherein the rivet is not deformed to connect the rings, except by the welding.

4. A method as in claim 1 wherein the rivet holes are located in front and rear ears extending from each of the rings.

5. A method as in claim 1 wherein the rings comprise an indent feature on one side which is sized and shaped for supporting a control cable, and wherein the mandrel comprises channels receiving the indent features.

6. A method as in claim 1 wherein the mandrel comprises a groove which slidably receives the head of the rivet.

7. A method as in claim 6 wherein the groove has different depths to thereby cam the rivet further into the holes as the rings are longitudinally slid on the mandrel.

8. A method comprising:
    placing a first endoscope deflection frame ring on a mandrel;
    inserting a rivet into a rivet hole of the first ring, wherein a head of the rivet is located at an interior side of the inner ear, wherein the head of the rivet is located in a groove of the mandrel;
    placing a second endoscope deflection frame ring on the first ring, wherein a rivet hole of the second ring is aligned with the rivet hole of the first ring;
    sliding the rings and the rivet on the mandrel to cause the rivet to move in the rivet hole of the second ring; and
    fixedly connecting the rivet to the second ring.

9. A method as in claim 1 the mandrel has a groove, and wherein the cam feature is located in the groove, where the cam feature cams the rivet in the groove to move the rivet in an outward direction.

* * * * *